(12) United States Patent
Millett et al.

(10) Patent No.: US 8,956,369 B2
(45) Date of Patent: Feb. 17, 2015

(54) PARALLEL DRILL GUIDE

(71) Applicant: Arthrex, Inc., Naples, FL (US)

(72) Inventors: Peter J. Millett, Vail, CO (US); Gregory A. Guederian, Naples, FL (US); Thomas Dooney, Jr., Naples, FL (US); Steven L. Vandermeulen, Ft. Myers, FL (US)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 13/661,784

(22) Filed: Oct. 26, 2012

(65) Prior Publication Data

US 2013/0046312 A1    Feb. 21, 2013

Related U.S. Application Data

(62) Division of application No. 12/758,387, filed on Apr. 12, 2010, now Pat. No. 8,308,732.

(60) Provisional application No. 61/168,517, filed on Apr. 10, 2009.

(51) Int. Cl.
*A61B 17/17* (2006.01)

(52) U.S. Cl.
CPC .................. *A61B 17/1728* (2013.01)
USPC ........................................ 606/96

(58) Field of Classification Search
USPC ............... 606/86 R, 96, 97, 98, 104
See application file for complete search history.

(56) References Cited

U.S. PATENT DOCUMENTS

| | | | | |
|---|---|---|---|---|
| 3,835,849 A | * | 9/1974 | McGuire | 606/96 |
| 4,549,538 A | * | 10/1985 | Schadrack et al. | 606/104 |
| 4,883,048 A | * | 11/1989 | Purnell et al. | 606/96 |
| 4,911,153 A | * | 3/1990 | Border | 606/98 |
| 5,141,513 A | * | 8/1992 | Fortune et al. | 606/96 |
| 5,330,468 A | * | 7/1994 | Burkhart | 606/96 |
| D357,534 S | * | 4/1995 | Hayes | D24/140 |
| 5,851,207 A | | 12/1998 | Cesarone | |
| 6,120,511 A | | 9/2000 | Chan | |
| D433,506 S | * | 11/2000 | Asfora | D24/140 |
| 6,342,056 B1 | * | 1/2002 | Mac-Thiong et al. | 606/96 |
| 7,488,326 B2 | * | 2/2009 | Elliott | 606/96 |
| 2002/0042605 A1 | * | 4/2002 | Castaneda et al. | 606/1 |
| 2007/0270845 A1 | | 11/2007 | Watanabe et al. | |
| 2008/0132900 A1 | | 6/2008 | Prien et al. | |

FOREIGN PATENT DOCUMENTS

WO    WO 01/82804 A1    11/2001

OTHER PUBLICATIONS

Smith & Nephew "6.5mm and 4.0mm Cannulated Screws"; Surgical Technique; 2008; pp. 12-13.
Synthes "4.5mm Cannulated Screws. Part of the Synthes Cannulated Screw System," Technique Guide; 2008; pp. 6.
Stryker Asnis ™III; "Cannulated Screw System"; Operative Technique; 2008; pp. 13.

* cited by examiner

*Primary Examiner* — Christian Sevilla
(74) *Attorney, Agent, or Firm* — Dickstein Shapiro LLP

(57) ABSTRACT

A parallel drill guide and system which maintains contact on the bone at various angles. The parallel drill guide comprises a fixed sleeve and a parallel, axially slidable, sleeve for guiding the insertion of two parallel wires or pins into bone at any angle while maintaining contact between the bone and the guide. The drill guide is also provided with a locking mechanism that locks the slidable sleeve into position at any lateral distance relative to the fixed sleeve, using a novel off-axis locking device.

7 Claims, 9 Drawing Sheets

PARALLEL DRILL GUIDE

CROSS-REFERENCE TO RELATED APPLICATIONS

This application is a divisional of application Ser. No. 12/758,387, filed Apr. 12, 2010, now U.S. Pat. No. 8,308,732, which claims the benefit of U.S. Provisional Application Ser. No. 61/168,517, filed on Apr. 10, 2009, the disclosures of which are hereby incorporated by reference in their entirety.

FIELD OF THE INVENTION

The present invention is directed to surgical instruments and, particularly, to a parallel drill guide used in arthroscopic procedures.

BACKGROUND OF THE INVENTION

Known drill guides are designed to place guide wires parallel into bone. These known parallel drill guides maintain contact on the bone only when positioned about perpendicular to the bone. Drill guides should desirably maintain contact on the bone to protect the soft tissue surrounding the bone.

A drill guide, system and method which would maintain contact on the bone while placing parallel guide wires and screws into the bones at various angles (i.e., other than about 90 degrees) for use in surgical procedures are needed.

SUMMARY OF THE INVENTION

The present invention provides a parallel drill guide and system which maintains contact on the bone while placing parallel guide wires and screws into the bone at various angles (other than about 90 degrees). The parallel drill guide comprises a fixed sleeve and a slidable or telescoping sleeve that allows the user to place two parallel wires or screws at any angle while maintaining contact between the bone and the guide. The drill guide is also provided with a locking mechanism that locks the slidable sleeve into position at a desired lateral distance relative to the fixed sleeve, using a novel off-axis locking device. The parallel drill guide sets and maintains any desired lateral distance between the sleeves. The parallel drill guide delivers guide wires, drills and/or parallel screws at any angle while maintaining contact of the parallel sleeves to the bone.

The parallel drill guide includes a body with an opening and a fixed sleeve passing through the opening and fixed to the body. The drill guide also includes a cannulated guide coupled to the body and passing through the opening. The slidable sleeve is able to slide axially through the cannulation of the guide, such that when the slidable sleeve is within the guide, the longitudinal axis of the slidable sleeve is substantially parallel to the longitudinal axis of the fixed sleeve.

The fixed sleeve of the drill guide has a circular cross section and the body is elliptical in shape. The opening has an elliptical shape.

The cannulated guide is preferably movable within the opening of the body of the drill guide, and the drill guide includes a locking device coupled to the body and the guide for securing the guide in a desired position relative to the fixed sleeve.

The invention also includes a method of surgery using the above-described parallel drill guide. The method includes the step of sliding a slidable sleeve through the cannulation of the guide so that the longitudinal axis of the slidable sleeve is substantially parallel to the longitudinal axis of the fixed sleeve. Next, the end of the fixed sleeve is placed against a bone and the end of the slidable sleeve is placed against the bone. When the angle between the fixed sleeve and the bone changes, the slidable sleeve slides through the cannulation of the guide so that the fixed and slidable sleeves maintain contact with the bone.

The method further includes placing drill pins or wires through the fixed and slidable sleeves and attaching the drill pins or wires to the bone, so screws can be inserted over the drill pins or wires into the bone.

The method may further comprise adjusting the lateral distance between the slidable sleeve and the fixed sleeve by using a locking device in the drill guide that is coupled to the body and the movable guide and is able to lock the guide at a distance from the fixed sleeve.

These and other features and advantages of the invention will be more apparent from the following detailed description that is provided in connection with the accompanying drawings and illustrated exemplary embodiments of the invention.

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art.

The present invention provides a parallel drill guide which maintains contact on the bone while placing parallel guide wires and screws into the bone at various angles (i.e., other than about 90 degrees). The parallel drill guide includes a fixed sleeve and a parallel slidable or telescoping sleeve that allow the user to place two parallel wires or screws at any angle while maintaining contact between the bone and the guide.

Preferably, the drill guide is also provided with a locking mechanism that locks the sleeves into position at any lateral distance relative to each other, using a novel off-axis locking device. The off-axis locking device of the parallel drill guide is capable of setting and maintaining any desired lateral distance between the sleeves. The parallel drill guide delivers guide wires, drills and/or parallel screws at any angle while maintaining contact of the two parallel sleeves to the bone.

Figure 1:
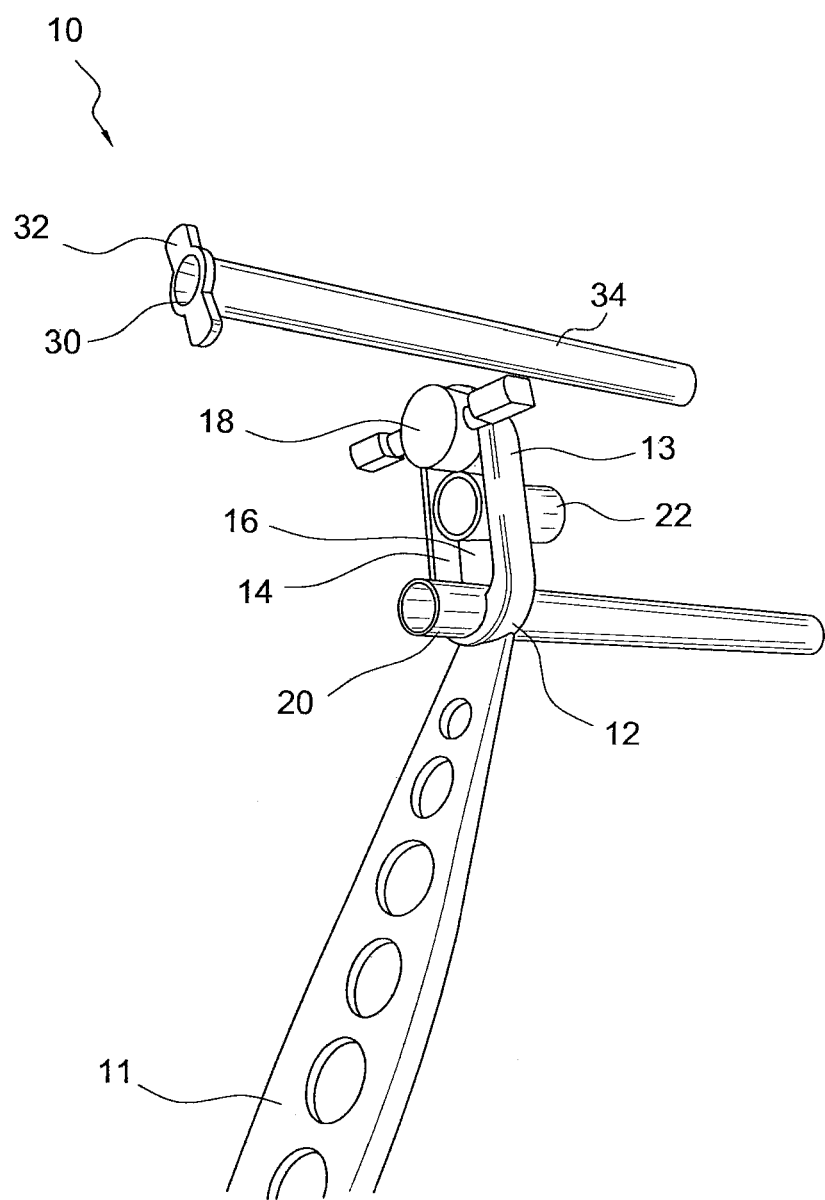
FIG. 1 illustrates a perspective view of a parallel drill guide.

Referring now to the drawings, where like elements are designated by like reference numerals, FIG. 1 illustrates a parallel drill guide 10. The guide 10 includes a handle 11 attached to a body or sliding block 12. The body 12 has an elliptical shape and a first side bar 13 and a second side bar 14 that are connected to form an elliptical opening 16. In another embodiment, the body 12 has a rectangular or other shape. An off-axis locking device 18 is coupled to the body.

Parallel drill guide 10 also includes a fixed sleeve 20 and laterally movable or translating cannulated guide 22. Both the fixed sleeve 20 and guide 22 have circular cross sections. The sleeve 20 and the guide 22 extend through the opening 16 of the body 12. The sleeve 20 and the guide 22 are positioned in the opening so that the sleeve 20 is about parallel to the guide 22 and the sleeve 20 and the guide 22 remain about parallel when the guide 22 translates or moves laterally. The translating cannulated guide 22 is also coupled to the axis locking device 18. The drill guide 10 further includes a slidable sleeve 30 that comprises a cannulated shaft 34 coupled to an end piece 32. The slidable sleeve 30 is of a dimension enabling it to slide through guide 22. Sleeve 30 also has a circular cross section with dimensions similar to those of fixed sleeve 20.

Figure 2A:
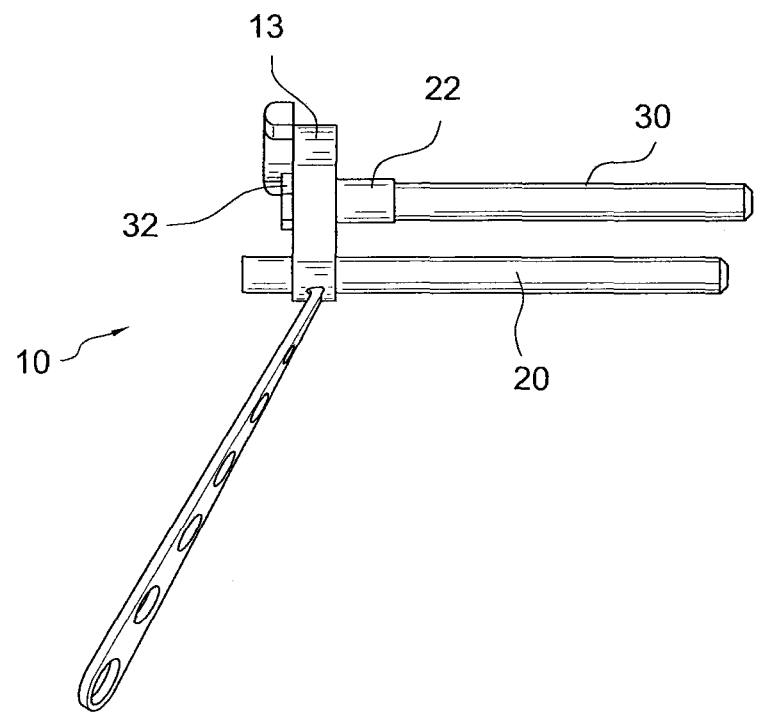
FIGS. 2a and 2b illustrate a slidable sleeve of the drill guide of FIG. 1.
Figure 2B:
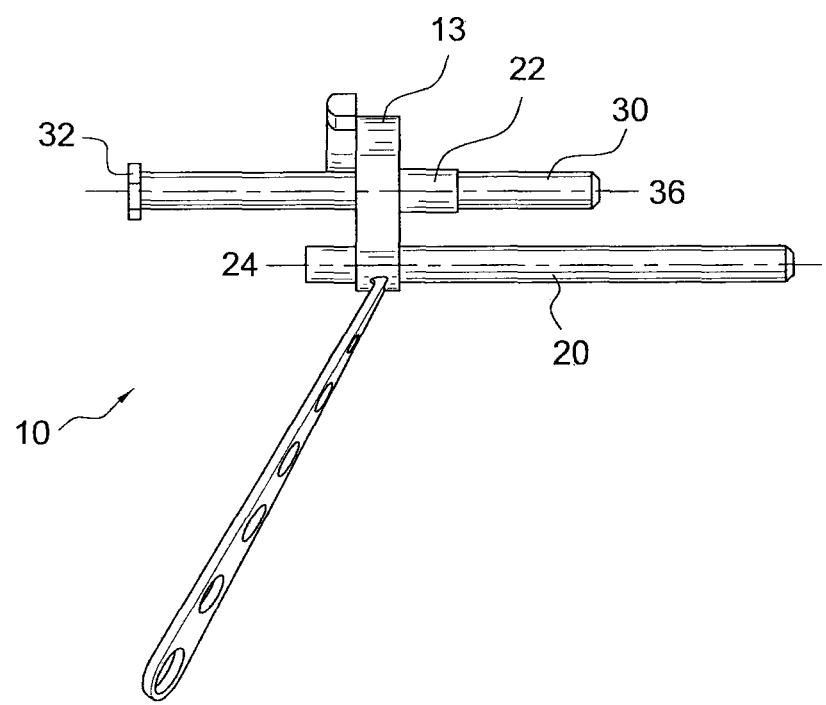

FIGS. 2a and 2b illustrate the slidable sleeve 30 sliding through guide 22. FIG. 2a illustrates the slidable sleeve 30 housed within the guide 22. In FIG. 2a, the end piece 32 of the slidable sleeve 30 is in contact with the guide 22 and the cannulated shaft 34 is housed within the guide 22 and extends away from guide 22. The end piece 32 prevents the sleeve 30 from slidable completely through guide 22 in one direction. When the sleeve 30 is within the guide 22, the longitudinal axis 36 of sleeve 30 is substantially parallel to the longitudinal axis 24 of fixed sleeve 20. FIG. 2b illustrates the slidable sleeve 30 partially extended through guide 22.

Figure 3A:
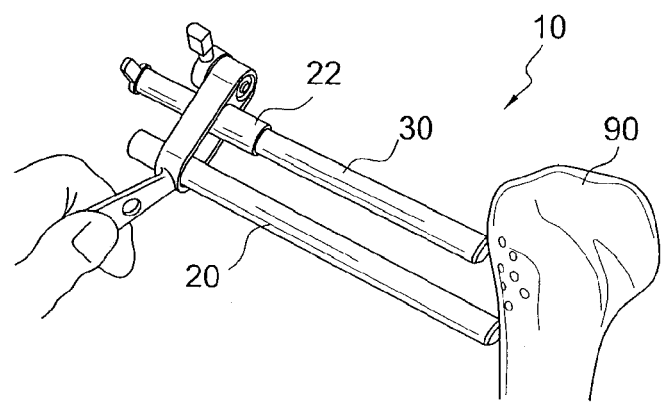
FIGS. 3a-c illustrate the drill guide of FIG. 1 positioned on the bone at different angles.
Figure 3B:
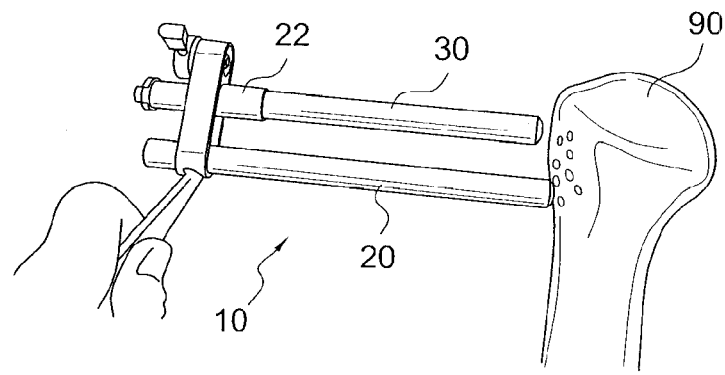
Figure 3C:
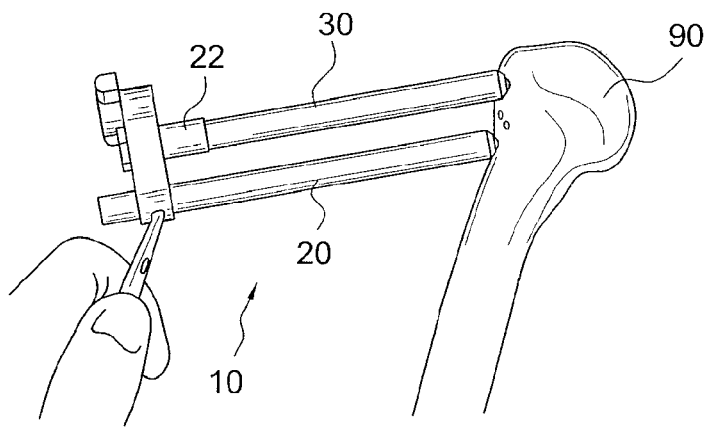

FIGS. 3a-c illustrate the drill guide 10 in varying positions next to a bone 90 so that the fixed sleeve 20 and the slidable sleeve 30 form varying angles with the surface of the bone 90. FIGS. 3a-c also illustrate how slidable sleeve 30 is maintained substantially parallel to the fixed sleeve 20 at the varying angles. FIG. 3a illustrates the drill guide 10 positioned relative to the bone 90 so that longitudinal axes of sleeves 20, 30 form an acute angle with the surface of the bone 90. The fixed sleeve 20 and the slidable sleeve 30 are both in contact with the bone 90, with the sleeve 20 substantially parallel to the sleeve 30.

FIG. 3b illustrates the drill guide 10 positioned relative to the bone 90 so that longitudinal axes of sleeves 20, 30 are perpendicular to the surface of the bone 90. Again, the fixed sleeve 20 and the slidable sleeve 30 are both in contact with the bone 90 and the sleeve 20 is still substantially parallel to the sleeve 30.

FIG. 3c illustrates the drill guide 10 positioned relative to the bone 90 so that a longitudinal axes of sleeves 20, 30 form an obtuse angle with the surface of the bone 90. Here, the fixed sleeve 20 and the slidable sleeve 30 are again both in contact with the bone 90 and the sleeve 20 remains substantially parallel to the sleeve 30.

FIGS. 3a-c also illustrate how the slidable sleeve 30 slides within the guide 22 to maintain contact with the bone 90. FIG. 3a illustrates the sleeve 30 with the end piece 34 extend away from the guide 22. In FIG. 3b, the sleeve 30 has slid within the guide 22 so that the end piece 34 is closer to the guide 22 to maintain in contact with the bone 90. In FIG. 3c, the sleeve 30 has slid within the guide 22 so that the end piece is in close proximate or touching the guide 22 to maintain in contact with the bone 90. In this manner, the sleeve 30 telescopes or slides so that when the sleeves 20, 30 are positioned on a bone 90 at varying angles the sleeves 20, 30 are maintained in contact with bone 90 and substantially parallel to one another.

Figure 4A:
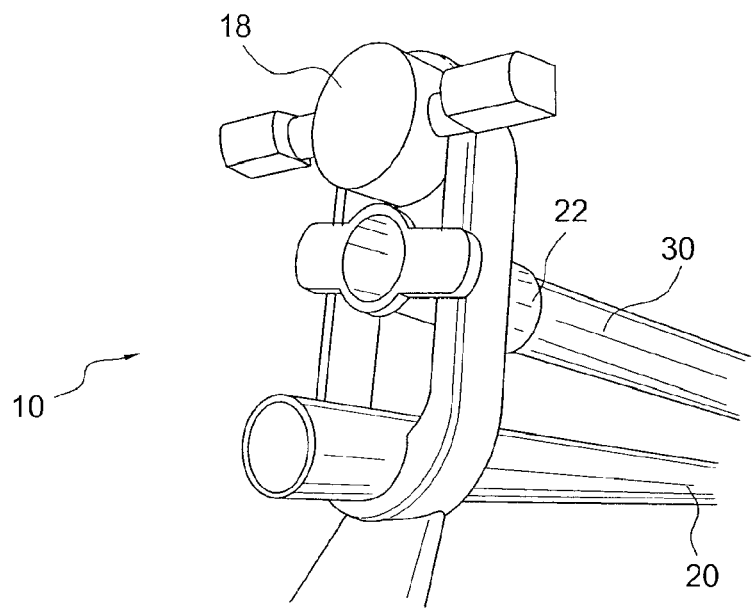
FIGS. 4a and 4b illustrate the slidable sleeve of the drill guide of FIG. 1 in a first position.
Figure 4B:
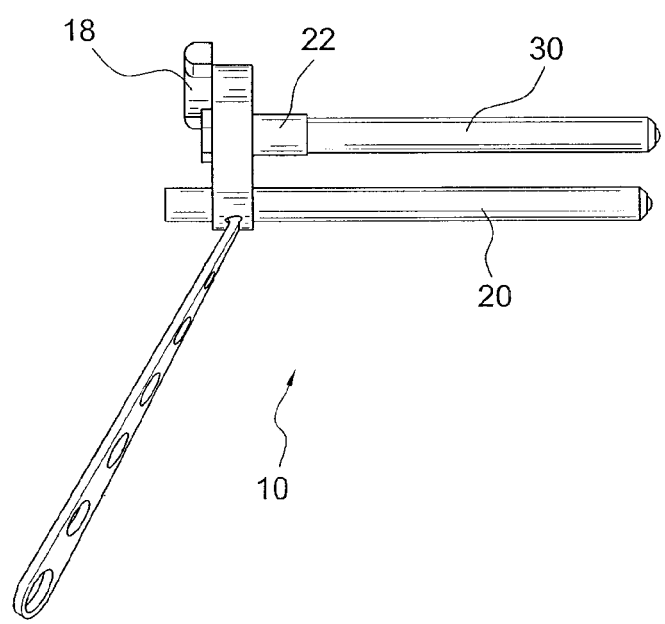
Figure 5A:
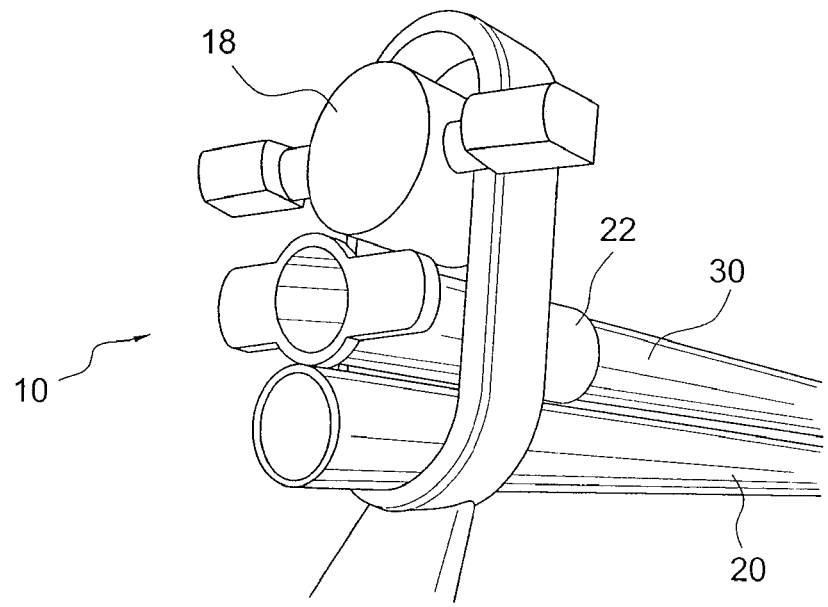
FIGS. 5a and 5b illustrate the slidable sleeve of the drill guide of FIG. 1 in a second position.
Figure 5B:
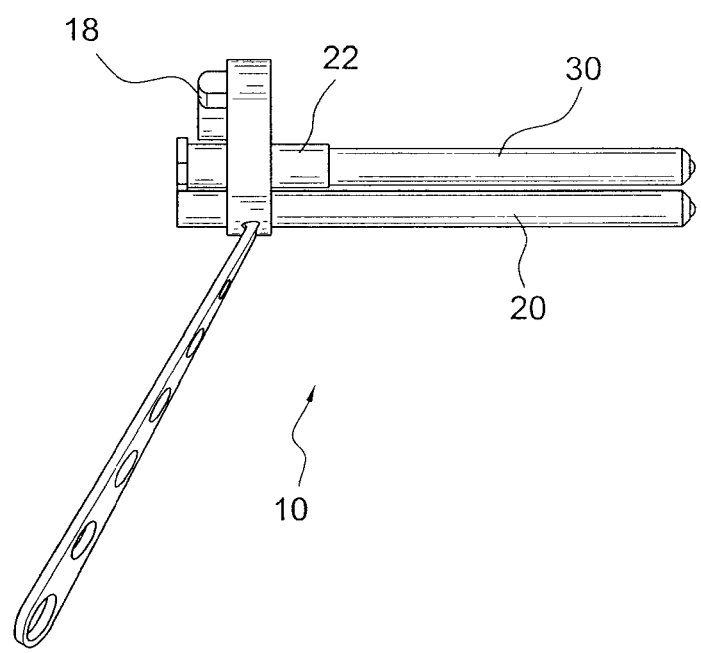

FIGS. 4a and 4b show slidable sleeve 30 and guide 22 in a first position relative to the fixed sleeve 20. The sleeve 30 and guide 22 can be moved in the opening 16 of the body 12 relative to the fixed sleeve 20. The axis-locking device 18 secures the guide 22 into a position. If the guide 22 needs to be positioned closer or farther from the fixed sleeve 20 the axis-locking device 18 is adjusted and the guide can be moved to a new position. FIGS. 5a and 5b show guide 22 in a position closer to the fixed sleeve 20, than the position of the guide 22 shown in FIGS. 4a and 4b. Using the axis locking device 18, the fixed sleeve 20 and the guide 22 can be locked into position at any lateral distance relative to each other. Importantly, regardless of the position of the guide 22. the fixed sleeve and the slidable sleeve 30 within the guide 22 will maintain a parallel relationship.

Figure 6A:
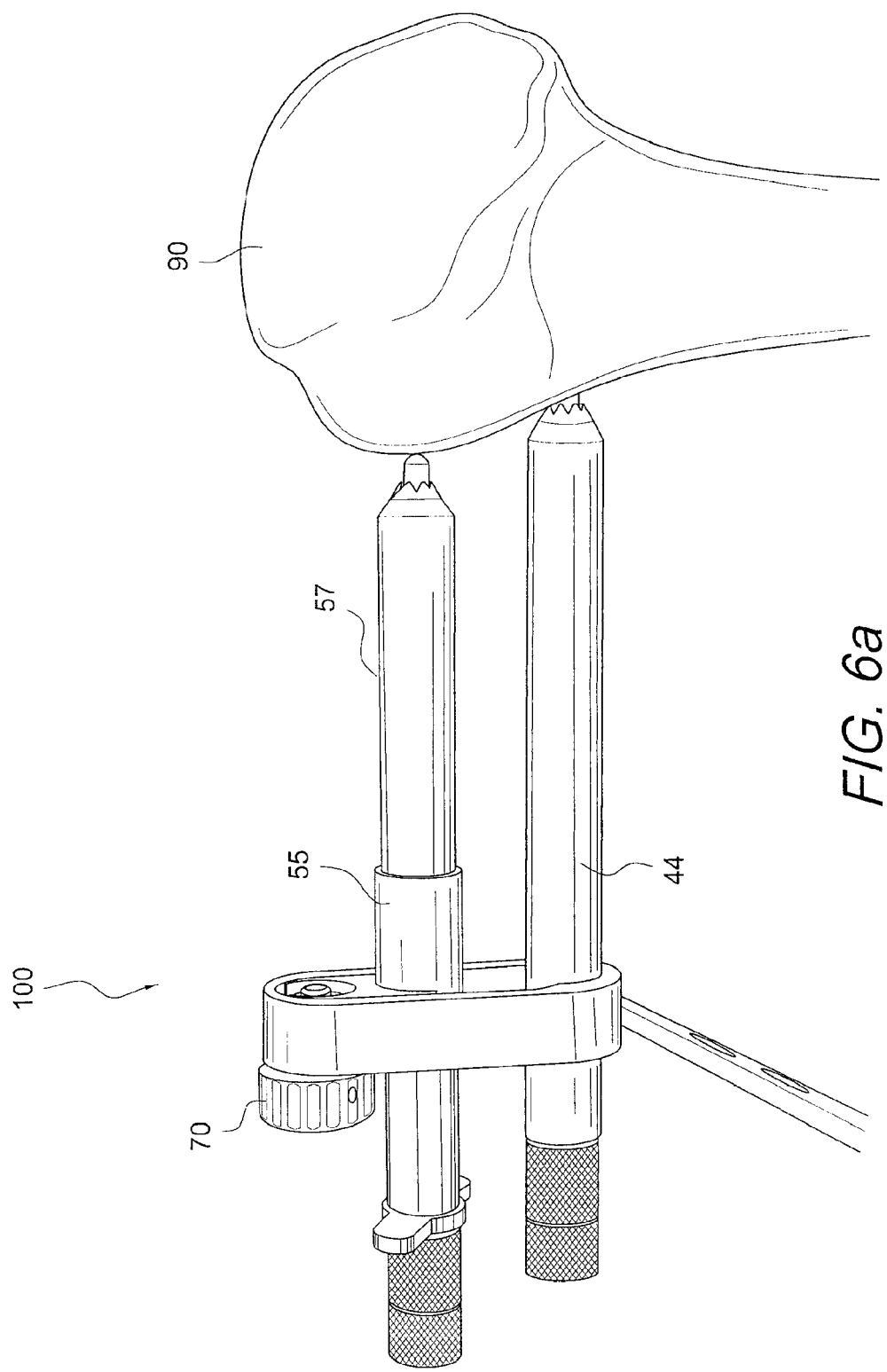
FIGS. 6a-c illustrate another embodiment of a drill guide positioned on the bone at different angles.
Figure 6B:
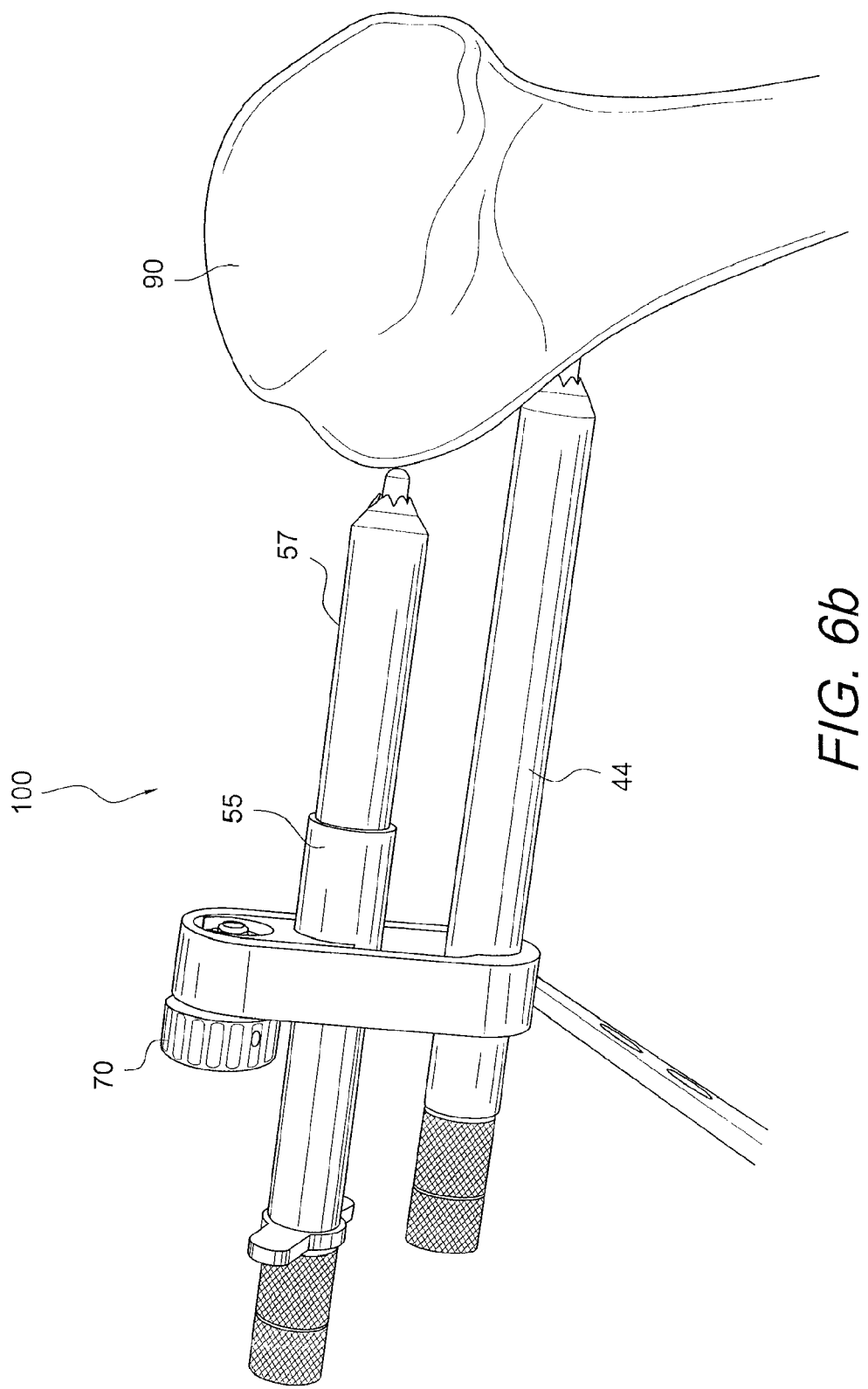
Figure 6C:
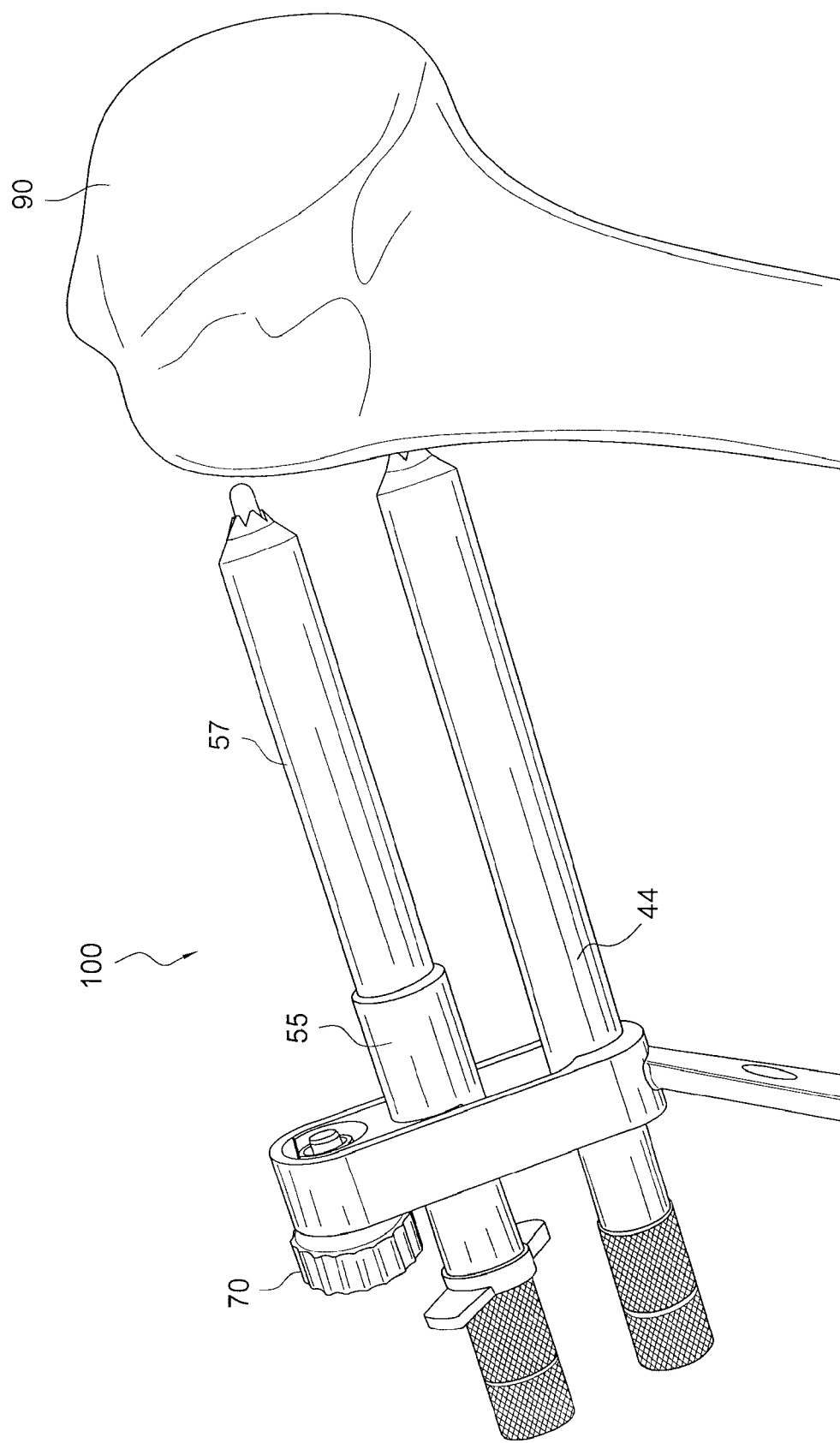

In another embodiment, FIGS. 6a-c illustrate a parallel drill guide 100 positioned on the bone 90 at different angles. The parallel drill guide 100 includes a fixed sleeve 44 and a laterally translating or movable guide 55 (with a clearance between 10-20 mm) which is about parallel to the fixed sleeve 44. The translating guide 55 of the parallel drill guide 100 translates or moves laterally relative to the fixed sleeve 44 while both sleeve 44 and sleeve 57, within guide 55, maintain contact to the bone 90 and are in a parallel orientation relative to each other. Sleeve 57 slides axially to keep the sleeves 44 and 57 parallel and against the bone at any angle.

Figure 7:
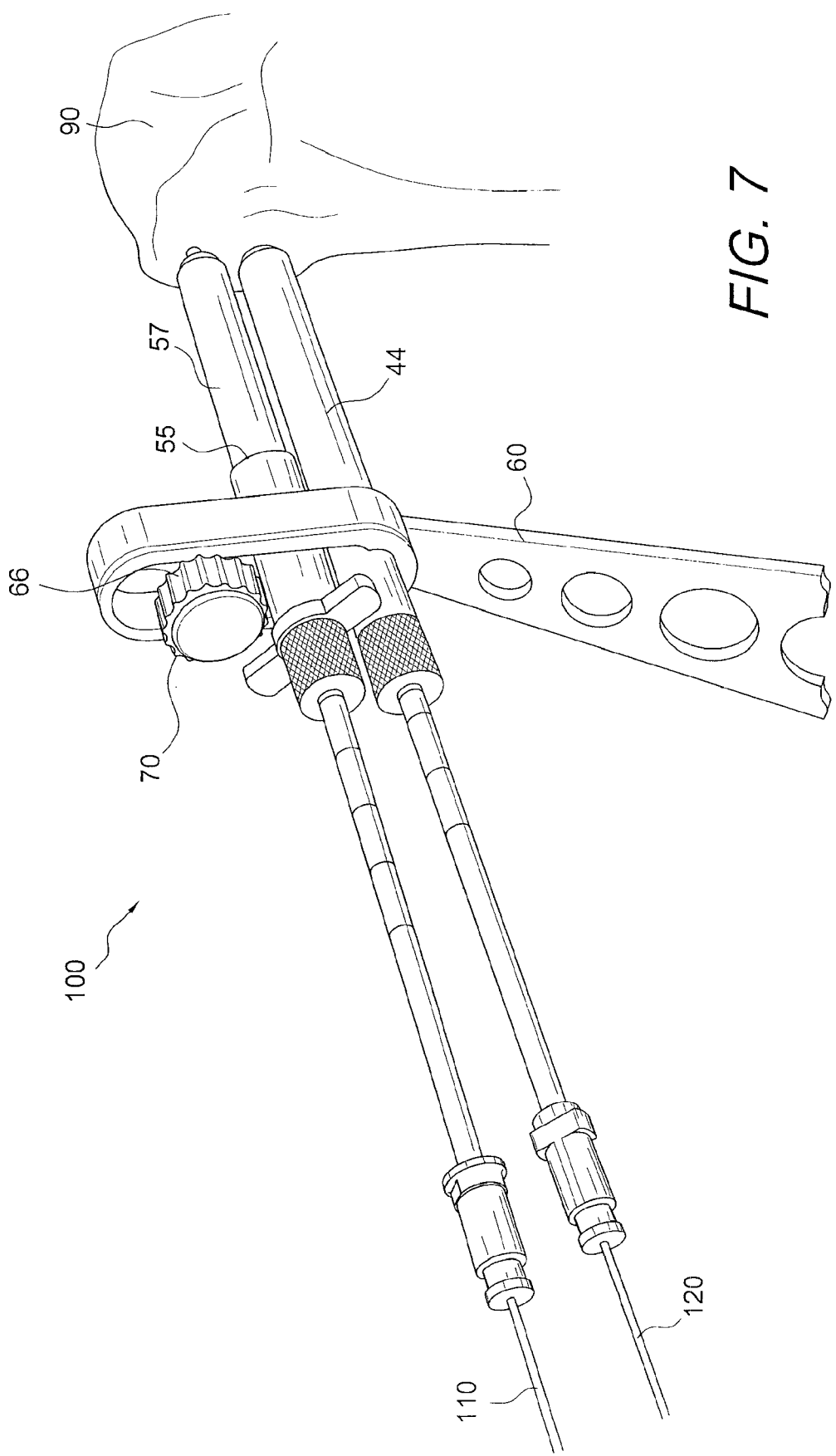
FIG. 7 illustrates the drill guide of FIGS. 6a-c being used with drill pins.

A method for using the parallel drill guide 100 is now explained with reference to FIG. 7. First, the desired distance between the holes or screws in a bone must be determined. Once determined, the drill guide 55 is adjusted and when the desired lateral distance between the sleeve and the guide has been reached, the translating drill guide 55 is tightened down with locking device 70 (for example, a twist knob 70 as shown in FIG. 7). Next, a drill sleeve 57 is placed within the drill guide 55. Alternatively, the drill sleeve 57 can be placed within the drill guide 55 and then the drill guide 55 and sleeve 57 are moved to the desired location relative to the sleeve 44. Next, drill pins 110, 120 are advanced through the drill sleeves 44, 57, respectively, and into the bone 90. Alternatively, wires can be advanced through the drill sleeves 44, 57 and into the bone 90. Screw lengths are determined and then cut-to-length screws are inserted over the parallel pins 110, 120 and into the bone.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting.

What is claimed as new and desired to be protected by Letters Patent of the United States is:

1. An apparatus for surgery comprising:
   a body with an elongated opening;
   a handle attached to the body;
   a fixed sleeve having a longitudinal axis and passing through the opening in the body and being fixed to the body, an end of the fixed sleeve being configured to be placed against a surface of a bone;
   a cannulated guide coupled to the body and passing through the opening in the body in a spaced apart, parallel relationship with respect to the fixed sleeve, the cannulated guide being laterally movable within the opening of the body; and
   a slidable sleeve able to slide through the cannulation of the guide, wherein, when a portion of the slidable sleeve is within the guide, a longitudinal axis of the slidable sleeve is substantially parallel to a longitudinal axis of the fixed sleeve, and wherein, when an end of the slidable sleeve being placed against the surface of the bone at an angle, and when the angle between the fixed sleeve and the bone changes, the slidable sleeve slides through the cannulation of the guide so that the fixed and slidable sleeves maintain contact with the bone, and the fixed sleeve remains parallel to the slidable sleeve regardless of the angle of the longitudinal axes of the fixed and slidable sleeves relative to the surface of the bone.

2. The apparatus of claim 1, wherein the body is elliptical in shape.

3. The apparatus of claim 1, wherein the opening has an elliptical shape.

4. The apparatus of claim 1, further comprising a locking device coupled to the body and the guide and able to securely fix the guide in a position relative to the fixed sleeve.

5. The apparatus of claim 4, wherein the locking device is an off-axis locking device.

6. The apparatus of claim 4, wherein the fixed sleeve is fixed to a side of the opening.

7. The apparatus of claim 6, wherein the guide is movable between the fixed sleeve and an opposite side of the opening.

\* \* \* \* \*